United States Patent [19]

Etherington et al.

[11] Patent Number: 4,552,155
[45] Date of Patent: * Nov. 12, 1985

[54] DIAGNOSTIC SPECIMEN COLLECTOR

[75] Inventors: Roger F. Etherington, Newport Beach; Clayton L. Ester, Sepulveda, both of Calif.

[73] Assignee: Transmed Corporation, San Diego, Calif.

[*] Notice: The portion of the term of this patent subsequent to Mar. 23, 1999 has been disclaimed.

[21] Appl. No.: 360,438

[22] Filed: Mar. 22, 1982

Related U.S. Application Data

[62] Division of Ser. No. 35,728, May 3, 1979, Pat. No. 4,320,770.

[51] Int. Cl.$^4$ .................... A61B 5/14; A61B 10/00
[52] U.S. Cl. .................... 128/766; 128/765; 604/222; 222/548
[58] Field of Search ............ 128/760, 763, 765–766; 604/188, 199, 208–211, 213, 222, 265–266, 268–269; 222/548

[56] References Cited

U.S. PATENT DOCUMENTS

| | | | |
|---|---|---|---|
| 2,875,761 | 3/1959 | Helmer et al. | 604/210 |
| 3,934,586 | 1/1976 | Easton et al. | 604/208 |
| 3,977,574 | 8/1976 | Thomas | 604/209 X |
| 4,004,575 | 1/1977 | Sarstedt | 128/675 |
| 4,043,336 | 8/1977 | Kreb, III | 128/766 X |
| 4,065,360 | 12/1977 | Kreb, III | 128/765 X |
| 4,320,770 | 3/1982 | Etherington et al. | 128/765 X |
| 4,370,987 | 2/1983 | Bazell et al. | 128/760 |
| 4,373,535 | 2/1983 | Martell | 128/765 |

FOREIGN PATENT DOCUMENTS

| | | | |
|---|---|---|---|
| 3018262 | 11/1981 | Fed. Rep. of Germany | 128/766 |
| 0087197 | 5/1966 | France | 128/763 |

Primary Examiner—Lee S. Cohen
Assistant Examiner—Angela D. Sykes
Attorney, Agent, or Firm—William F. Frank

[57] ABSTRACT

A device for taking specimens for laboratory analysis, specimens being of a fluid type such as body liquids or may be liquids of a different source. The device comprises a hollow body member with a closed end and an open end. The closed end has orifice therethrough which orifice is eccentric with respect to the longitudinal axis of the body member. A plunger having a plunger tip means is inserted into the body member for the purpose of accurately varying the internal volume of the device. The closed end is provided with an exteriorly mounted closure which may be of a rotatable type or a sliding plate type. The closure contains an orifice which may be aligned with the orifice in the closed end to take specimens into the device and then the closure may be moved with reference to the body member to misalign the orifices so that the orifice in the body member is closed and the specimen cannot be ejected from the device. Sealing means are provided between the closure interior and the exterior of the closed end around the orifice in the body member. The present embodiment of the invention includes the presence of an agent which is applied to the collected specimen for the purpose of maintaining it, culturing it, or defining the composition of the specimen. The agent may be placed on the interior of the hollow body member in which configuration it contacts the specimen immediately upon the entry of the specimen into the hollow body. The agent may be placed in a recess on the interior of the closure which recess is brought into registration with the orifice in the closed end only by movement of the closure so there is subsequent contact between the agent and the specimen. This avoids any communication between the specimen source and the specimen agent or specimen after its contact with the agent. There is also disclosed a novel plunger having a pivotal member on the stem of the plunger which engages the open end of the hollow body member of any type of syringe to prevent accidental ejection of a collected specimen.

7 Claims, 10 Drawing Figures

DIAGNOSTIC SPECIMEN COLLECTOR

This application is a division of Ser. No. 035,728 filed May 3, 1979, now U.S. Pat. No. 4,320,770.

FIELD OF THE INVENTION

The present invention is in the field of medical diagnostic devices, and more particularly, in that portion of this field in which fluid specimens are collected for subsequent analysis in a laboratory.

BACKGROUND OF THE INVENTION AND PRIOR ART

The taking of fluid specimens for laboratory analysis is an important diagnostic tool in the treatment of medical diseases and ailments. It is clearly evident that specimens should be as free as possible from any possible secondary contamination, be it from the area from which the specimen is taken or the ambient conditions external to the subject but through which the specimen collecting device must be moved. Conventionally, fluid specimens are withdrawn from a subject by syringe, having generally a hypodermic needle attached thereto for penetration of the subject. Often there is a need to introduce the collected specimen to a specimen maintenance agent, reagent, or culture media to induce specimen growth, specimen identification, or sustain the collected specimen's values constant and viable for subsequent laboratory procedures. It is not generally desired to introduce the specimen agent, reagent, or culture media, nor a specimen to which any of these media have been applied to a patient, the matter of toxicity being the question. Specimens may be body liquids such as blood or urine, or other tissue fluids, or may be anaerobic specimens collected from various organs within the body, or may consist of water or other non-body fluids.

In some institutions, the practice has been to place a cork or stopper over the end of the needle after it is withdrawn from the subject in order to seal and protect the collected specimen, and then the syringe is carried to the laboratory. In other situations, the syringe collected specimen is injected through a rubber stopper into an otherwise sealed vial or tube. These vials and tubes often containing a specimen agent are then sent to the laboratory.

Sometimes, a specimen is ejected from the syringe into a tube containing specimen maintenance media which tube is then closed and taken to the laboratory, sealing and maintenance of the specimen being of primary importance in preserving the viability of the specimen and its quantitative values.

In attempts to increase the viability of the specimen and further minimize secondary contamination, there has been developed a vacuum operated system for taking liquid samples. The system comprises a bottle often containing a specimen maintenance or culture medium which is evacuated and then sealed with a rubber diaphragm to maintain the negative pressure within the container. To use such a device, use is made of a special hypodermic needle which may be considered as double ended. One of the needles is inserted into the subject and the other end of the needle is then inserted through the rubber diaphragm. The negative pressure in the container automatically draws fluid into the container. The draw is sudden and uncontrollable, and has been known to cause veins to collapse. Also, the vacuum within the container may be less than necessary to withdraw the desired amount of fluid. Because the interior volume of such containers cannot be variably controlled, such containers are made available in many capacity sizes such as 5, 7, 10, 15, and 20 cc capacities, resulting in the need to stock many sizes of the containers to meet varying requirements. Many of these types of containers are sold in a non-sterile state, and thus the institutions utilizing them must subject them to sterilization or run the risk of contaminated cultures. It has been noted that in many instances the autoclaving for sterilization reduces the amount of negative pressure within the container, and such containers do not provide the means to expel the fluid within them.

In the recent developments in the field of collecting devices, is a syringe type device which is shown in U.S. Pat. No. 4,043,336. This patent is a hollow body member with a plunger therein. The so-called closed end of the end portion of the body member has a circular disk adhesively secured near the closed end, but providing space for another disk between the secured disk and the interior surface of the closed end. The second disk contains a nipple which extends outwardly through a slot in the closed end. Both disks have an orifice in each, and each movement of the disk with the nipple in the slot and the closed end of the syringe brings the two orifices into communication or out of communication. This device may contain an exterior protrusion on the side of the body member into which may be placed some form of medium for automatic and instant application to the specimen as it is being collected. The design of this device does not provide for the separation of the self-contained specimen agent from the fluid in the chamber of the syringe.

SUMMARY OF THE PRESENT INVENTION

The present invention is an elongated hollow body open at one end and closed at the opposite end with an orifice in the closed end. A plunger with sealing means on one end is slidably inserted into the body to variate the interior volume while maintaining a sealing of the interior of the body. Movable one piece closure means are exteriorly mounted on the closed end of said body. The closure has an outwardly extending fitting, with an orifice therethrough, adapted to receive compatible fittings or medical collection devices such as needles or multiple specimen collecting devices or adaptors used on diagnostic equipment. The closure means can be moved from a position in which both the orifices are in communication so that a specimen can be drawn into the body and the closure means orifice, then moved out of communication so that the orifice in the closed end of the body is sealed. Sealing means for the orifice in the closed end are positioned around the orifice between the closed end of the body and the closure means to create a friction-free space between the closed end and the inner surface of the closure.

The invention also includes an agent or contacting the collected specimen which is placed in the closure member and brought into communication with the specimen that has been collected when the closure means has been moved to place the two orifices out of communication and bring the agent into communication with the orifice in the closed end of the body after the device is removed from the specimen source. This precludes any possibility of specimen with an agent being injected into a patient.

There also is included a novel plunger having a pivotal vertical member on the stem of the plunger which engages the open end of a body member of any type syringe after a specimen has been drawn into the body member.

The wall sections of the body member and the closure means can be of specially selected materials in a thickness to provide maximum protection from any possible oxygen gas permeation while the device is exposed to ambient conditions. The embodiments of the device of the present invention provide:

Devices of practical design and structure for the reasonable cost manufacture and assembly required of a disposable syringe.

Syringes have self-contained specimen agents for application to the specimen.

Syringes having self-contained specimen agents and providing protection to the patient or specimen source from cross-contamination with the self-contained specimen agent by preventing mixing of the specimen and the specimen agent until the syringe has been removed from communication with the specimen source.

A syringe having self-contained specimen agents and a plunger with graduated protective check-stops to minimize changes of patient or specimen source being reinjected with fluid that has already come in contact with the specimen agents. This novel plunger also provides volume indices.

Syringes having connector fittings compatible with what are commonly called "luer" fittings but not necessarily limited to such. It will be recognized that such a fitting could be used directly as the dispensing nozzle without additional nozzle means.

Syringes for containing a reconstitutable substrate in the recessed compartment of the cap (such as some antibiotics that are unstable in liquid form). That could be mixed with a proper liquid in the chamber of the syringe just prior to injection to the subject.

BRIEF DESCRIPTION OF THE DRAWINGS

The present invention is shown by way of illustration in the following drawing figures in which.

DETAILED DESCRIPTION OF THE INVENTION

Figure 1:
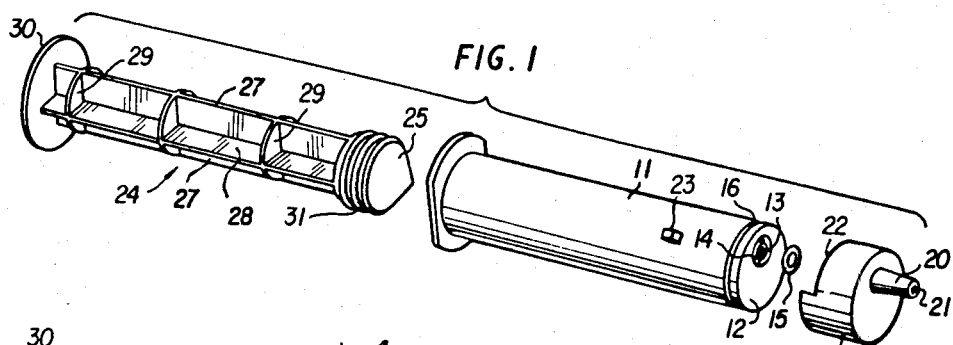
FIG. 1 is an exploded perspective view of the present invention.
Figure 9:
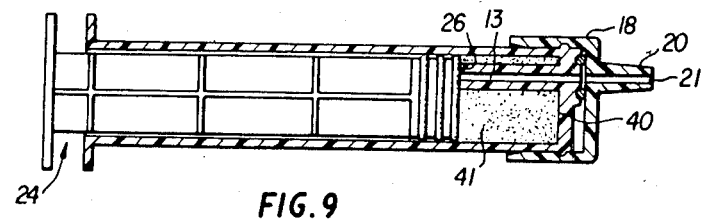
FIG. 9 is an elevation view in partial section of another embodiment of the invention as shown in FIG. 2.

Referring now to FIG. 1, the invention is seen to comprise a generally well-known type of syringe having a hollow cylindrical body 11 open at one end to receive a plunger 24 and having a substantially closed end 12 opposite the open end. The closed end 12 has an orifice 13 around which there is an annular recess 14 to receive an O-ring 15. Adjacent the closed end 12 is an annular recess 16 which receives an internal inwardly extending bead 17 in a one piece cap 18. It will be apparent that other concepts of movably retaining the closure on the closed end such as threads, bayonet mount and the like may be employed. The cap 18 has a skirt extension which forms an open end to be fitted over the closed end body 11 and rotate thereabout. The cap also has a closed end 19 from which there extends outwardly a cannula receiving member 20 having an orifice 21 therethrough. The cannula receiving member 20, hereinafter referred to as a nipple, is of a configuration which will receive a cannula of the conventional type and also will receive adaptors, known in the medical art, which will permit the use of a single venal puncture by cannula and the successive application of the syringes of the present invention for the purposes of taking a plurality of samples. These adaptors are normally configured with means therein to permit closure thereof after a sample has been taken so as to prevent exodus of any body fluid due to the pressure of the fluid within the human body. Fitted into hollow body member 11 is a plunger 24 of the type which is well known in the medical arts. Generally, it is configured with a plunger tip having a conical end surface 25 although the end surface may be flat 26 as shown in FIG. 9. The plunger tip is positioned on one end of a stem shown to consist of a pair of longitudinal members 27 and 28 arranged at right angles to each other along the axis of the plunger and along which are a plurality of circular disks 29. The plunger stem terminates in a thumb ring (not shown) or finger plate 30 opposite the plunger tip. In addition to the end surface 25 or 26, the plunger tip includes at least one annular ring 31, generally of a resilient material, which provides a sealing relationship with the interior wall of the hollow body member 11 to insure that the movement of the plunger 24 would not result in any fluid medium escaping by the plunger. These annular rings may be considered seals.

Figure 2:
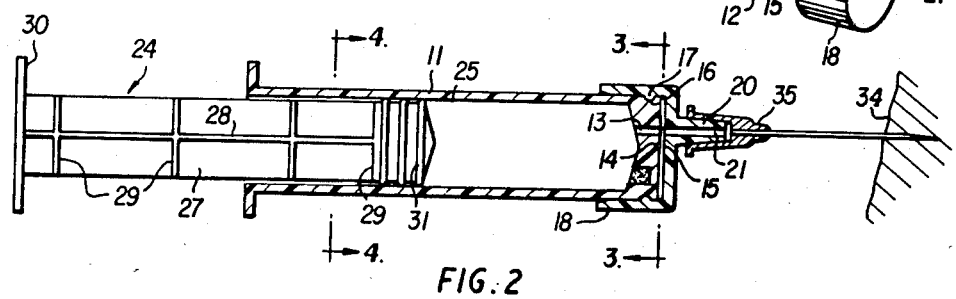
FIG. 2 is a partial cross-sectional view in elevation of the invention shown in FIG. 1 showing a specimen being collected.
Figure 3:
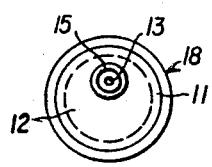
FIG. 3 is an elevation view along the section plane 3—3 in FIG. 2.

Referring now to FIG. 2, there is a showing of one embodiment of the invention preparatory to extracting a specimen. The plunger 24 has been partially withdrawn within the hollow body member 11 to collect the fluid specimen 33 which will come from a specimen source 34 via a conventional type cannula 35. In this figure it will be noted that the O-ring 15 seated in recess 16 has a portion extending outwardly from the closed end surface 12 into contact with the inner surface 36 of closed end 19 of cap 18, the extension thus preventing contact between closed end 12 and this inner surface. This extending portion of O-ring 15 forms a seal with the inner surface 36 of the cap 18, thus insuring that the fluid specimen enters only the interior of the hollow body member 11. Study of FIGS. 2 and 5 discloses that the extending portion of O-ring 15 in contact with inner surface 36 functions as a sealed bearing surface about which cap 18 rotates.

Figure 4:
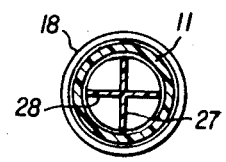
FIG. 4 is a cross-sectional view along section plane 4—4 in FIG. 2.

The cross-sectional view of FIG. 4 of the plunger 24 principally illustrates that the right angle position of the members 27 and 28 not only provides resistance to vertical and lateral flexing of the plunger, but the outer surfaces of these members also serve to provide bearing or guide surfaces for the plunger so that it is not displaced from its central axis sufficiently to destroy the vacuum created by the inner sealing members 31.

Figure 5:
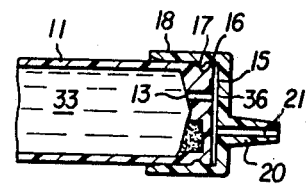
FIG. 5 is a partial cross-sectional view in elevation of the embodiment shown in FIG. 2 after the specimen has been collected.
Figure 6:
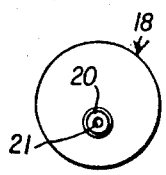
FIG. 6 is an end view in elevation of the embodiment shown in FIG. 5.

Referring now to FIG. 5, it will be seen that the cap 18 has been rotated through a given number of degrees in accordance with the length of the slot 22 in cap 18 as controlled by the stop member 23 on the outer surface of hollow body member 1 (see FIG. 11). This means for orienting the cap relative to the hollow member is configured so that the slot 22 permits movement of the cap 18 from the specimen collecting position shown in FIG. 2 to the position shown in FIG. 4 by a clockwise rotation of the body member 11 with respect to cap 18 when cap 18 is held. By such rotation, the portion of the inner surface 36 of cap 18 which does not contain the orifice 21 is placed over the passageway 13 in hollow body member 11, thus sealing it effectively. Other external and/or internal means may be substituted to indicate the orientation of the cap relative to the hollow member.

Figure 7:
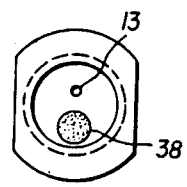
FIG. 7 is an elevation view of the left end of the syringe body shown in FIG. 2.

FIG. 2 shows that in the inner surface of closed end 12 of the hollow body member 11 there is a recess 37, shown in FIG. 7 to be circular, but which may have a rectilinear form into which is placed a substance 38 which is considered generally as an agent which reacts with the specimen being collected to maintain it or react with the fluid to develop a culture of the specimen or to react with the specimen to identify various substances in the specimen. The agent may be in the form of a liquid, solid, or a semi-solid such as a firm gel and can be of a composition well known in the art.

Figure 8:
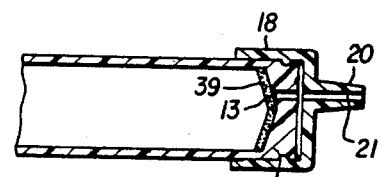
FIG. 8 is a partial elevation view in cross-section of a modification of the invention disclosed in FIG. 2.

In FIG. 8 there is seen a modification of the embodiment of the invention shown in FIG. 2 in that the agent 39 has been formed as a layer on the interior surface of the end wall 12 of the hollow body member.

Referring now to FIG. 9, there is seen another variation of the embodiment of the invention shown in FIG. 2 in that the interior wall of the closed end 12 of the hollow body member 11 now has a flat surface and the passageway 13 now extends through an inwardly extending tubular member 40 to form an annular recess in which the agent 41 is placed. In this embodiment, it will be noted that the end surface 26 of the plunger 24 has a flat surface which matches the interior surface of the closed end 12.

Figure 10:
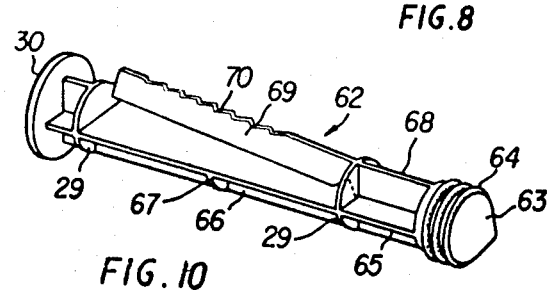
FIG. 10 is a perspective view of a novel plunger for use with the present invention.

FIG. 10 shows a novel plunger which selectively may be incorporated with the hollow body chamber of the present invention, or which may be used with other hollow body members unrelated to the present invention. A novel plunger 62 resembles to a great extent the plunger 24 shown in FIG. 1 in that it has a plunger tip having a tapered inner face 63 which contacts the matching tapered interior of a body chamber just as surface 25 in FIG. 1. It is provided with at least one annular resilient bead 64 providing sealing with an inner wall of a body chamber. It is also provided at the end opposite the tapered surface 63 with a gripping disk 30. Lying between the gripping disk 30 and the sealing ring 64 is a horizontal member 65 serving the same purpose as surface 28 in FIG. 1. Perpendicular to surface 63 is a vertical surface 66 which provides stability in the plunger against flexing. A plurality of disks 29 are provided as bearing surfaces for the plunger during its travel within a hollow body chamber. A semi-circular disk 67 is interposed on member 66 between the two disks 29. A short vertical member 68 is inserted between the sealing ring 64 and the first circular disk 29. Interposed between the two circular disks 29 is a vertically-pivotal member 69 which has a hinging action at its juncture with disk 29 to allow the member 69 to be depressed toward the horizontal member 65 for insertion of the plunger into a hollow body chamber. A plurality of notches or stepped surfaces 71 are provided on the outer surface of the member 69. The purpose of the notched surfaces is to provide a means on the plunger whereby after it has been withdrawn, thus drawing a specimen into the chamber, the notch will engage the outer ring 72 of the body chamber 11 and will hold the plunger against being pushed back towards the closed end of the chamber thus expelling the fluid. To permit the plunger to be pushed down into the hollow chamber, it would be necessary to depress member 69 towards horizontal member 65, thus disengaging the stepped surface 71 from contact with the holding ring 72. The stepped surfaces 71 may also have a length which by calibration would be an indication of a volume of specimen which has been withdrawn into the hollow body chamber.

What is claimed is:

1. A diagnostic specimen collector consisting of:
   an elongated hollow body open at one end and closed at the opposite end with a single orifice in said closed end;
   a plunger having sealing means on one end which is slidably inserted into, and in sealing relationship with, said body to vary the interior volume of said body;
   a closure for said closed end orifice consisting of a one-piece cap having an end wall with a skirt extension exteriorly mounted to encompass said closed end concentrically and rotatable thereabout and a nipple to receive compatible fittings of specimen taking medical devices extending outwardly from the outer surface of said end wall and an orifice in said closure passing axially through said nipple and said end wall, said closure being rotatable from a first position in which both orifices are out of communication and said closed end orifice is in a sealed condition to a second position in which both orifices are in sealed communication for the passage of a specimen upon movement of said plunger and back to said first position after passage of said specimen; and sealing means for the closed end orifice comprising an O-ring positioned concentrically with reference to said closed end orifice in an annular groove on an outer surface of said closed end, a portion of said O-ring extending above said closed end outer surface to create a friction-free space between said outer surface and a inner surface of said closure except for a moving area of sealing contact between said ring portion and the inner surface of the closure, said ring portion providing a bearing surface for said rotation of said closure and an agent for application to said specimen in the interior of said hollow body.

2. The collector according to claim 1 wherein said closure is positioned on said body by cooperating bead and annular recess means arranged on the exterior of the closed end and inner surface of said skirt extension.

3. The collector according to claim 1 wherein the axis of said orifice in said closed end is eccentric to the axis of said body and the orifice in said closure is eccentric to the central longitudinal axis of said closure.

4. The collector according to claim 1 wherein said sealing means comprises an annular bead formed integrally with said closed end around said closed end orifice.

5. The collector according to claim 1 wherein said agent is in a recess on an interior surface of said closed end.

6. The collector according to claim 1 wherein said agent is applied as a layer to an interior surface of said closed end.

7. The collector according to claim 1 wherein said plunger comprises a stem extending between said sealing means and a digital gripping member, a portion of said stem being deflectable relative to the axis of said stem to selectively engage said open end with one of a plurality of notched segments formed on an outer surface of said deflectable portion.

* * * * *